（12） United States Patent
Wang et al.

(10) Patent No.: US 11,386,248 B2
(45) Date of Patent: Jul. 12, 2022

(54) METHOD AND DEVICE FOR SIMULATING ATOMIC DYNAMICS

(71) Applicant: FUJITSU LIMITED, Kawasaki (JP)

(72) Inventors: Liuan Wang, Beijing (CN); Jun Sun, Beijing (CN)

(73) Assignee: FUJITSU LIMITED, Kawasaki (JP)

( * ) Notice: Subject to any disclaimer, the term of this patent is extended or adjusted under 35 U.S.C. 154(b) by 245 days.

(21) Appl. No.: 16/695,834

(22) Filed: Nov. 26, 2019

(65) Prior Publication Data

US 2020/0175126 A1    Jun. 4, 2020

(30) Foreign Application Priority Data

Nov. 29, 2018   (CN) .......................... 201811444034.4

(51) Int. Cl.
  *G06F 30/20*       (2020.01)
  *G06F 17/18*       (2006.01)
  *G06N 3/04*        (2006.01)

(52) U.S. Cl.
  CPC ............. *G06F 30/20* (2020.01); *G06F 17/18* (2013.01); *G06N 3/0454* (2013.01); *G06N 3/0472* (2013.01)

(58) Field of Classification Search
  CPC .......... G06F 30/20; G06F 17/18; G06F 30/25; G06F 30/27; G06F 30/28; G06F 2111/00; G06F 2119/22; G06N 3/0454; G06N 3/0472; G06N 3/08; G16C 10/00; G16C 20/70; G16C 20/80; G16C 99/00
  See application file for complete search history.

(56) References Cited

U.S. PATENT DOCUMENTS 9,373,059 B1 *   6/2016   Heifets ..................... G06T 1/60

FOREIGN PATENT DOCUMENTS

WO    WO 2019/098154 A1    5/2019

OTHER PUBLICATIONS

Han Wang, et al., "DeePMD-kit: A deep learning package for many-body potential energy representation and molecular dynamics," Computer Physics Communications 228 (2018) 178-184 (Year: 2018).*
Extended European Search Report dated Jun. 8, 2020 in related European Patent Application No. 19209742.6 (12 pages).
(Continued)

*Primary Examiner* — Steven W Crabb
(74) *Attorney, Agent, or Firm* — Staas & Halsey LLP (57) ABSTRACT

A method and a device for simulating atomic dynamics includes setting initial positions for multiple specific atoms in a specific scene; calculating, based on the initial positions, positions of the multiple specific atoms at each time in a first time series by utilizing a Large-scale Atomic/Molecular Massively Parallel Simulator (LAMMPS) configured with respect to the specific scene, as real positions; calculating, based on the initial positions, positions of the multiple specific atoms at the same time in the first time series by utilizing a generative adversarial network (GAN), as predicted positions; improving a configuration of the GAN based on the real positions and the predicted positions at a same time. Initial positions are settable for multiple atoms to be simulated in a scene; positions of the multiple atoms to be simulated are calculated at each time in a second time series in the scene by utilizing the improved GAN.

9 Claims, 7 Drawing Sheets

(56) References Cited

OTHER PUBLICATIONS

Wei Ouyang et al: "Deep learning massively accelerates super-resolution localization microscopy"; Nature Biotechnology, vol. 36, No. 5, Apr. 16, 2018; pp. 460-468, XP055697959, ISSN: 1087-0156, DOI: 10.1038/nbt.4106; (16 pages).
Zhaocheng Liu et al: "Simulating the Ising Model with a Deep Convolutional Generative Adversial Network"; ARXIV.ORG, Cornell University Library, 201 Olin Library Cornell University Ithaca, NY, 14853, Oct. 13, 2017 (Oct. 13, 2017); XP080828673; (7 pages).

\* cited by examiner

METHOD AND DEVICE FOR SIMULATING ATOMIC DYNAMICS

CROSS-REFERENCE TO RELATED APPLICATIONS

This application is based on and hereby claims priority under 35 USC 119 to Chinese Patent Application No. 201811444034.4, filed on Nov. 29, 2018, in the China National Intellectual Property Administration, the entire contents of which are incorporated herein by reference.

FIELD

The present disclosure relates to a method and a device for simulating atomic dynamics, and in particular to a method and a device for simulating atomic dynamics by utilizing a deep neural network.

BACKGROUND

Molecular dynamics simulation aims to study physical movements of atoms and molecules. With the development of computer technology, the molecular dynamics simulation and the application thereof is attracting increasing attention. On one hand, the molecular dynamics simulation can quantitatively explore mechanisms and laws in nature. On the other hand, the molecular dynamics simulation promotes research and development in an economic, efficient and predictable way.

Known tools for molecular dynamics simulation include a Large-scale Atomic/Molecular Massively Parallel Simulator (LAMMPS) developed by Sandia National Laboratory. The LAMMPS can support systems consisting of millions of atoms/molecules in gas, liquid and solid form. In the LAMMPS, a simulation domain is divided into small three-dimensional sub-domains by utilizing spatial decomposition technology, and each sub-domain is to be processed by a processor. In spite of this, simulation by the LAMMPS still requires a lot of computing resources and time.

In addition, methods based on deep neural network have been greatly developed in various applications in recent years. In these methods, the deep neural network is typically trained based on a data set, and then the trained deep neural network is deployed in actual applications.

SUMMARY

The present disclosure provides a solution where molecular dynamics simulation is performed by utilizing a deep neural network. According to a first aspect of the present disclosure, a method of simulating atomic dynamics is provided. The method includes: setting initial positions for multiple specific atoms in a specific scene; calculating, based on the initial positions, positions of the multiple specific atoms at each time in a first time series by utilizing an LAMMPS configured with respect to the specific scene, as real positions; calculating, based on the initial positions, positions of the multiple specific atoms at each time in the first time series by utilizing a generative adversarial network, as predicted positions; improving a configuration of the generative adversarial network based on the real position and the predicted position at the same time; setting initial positions for multiple atoms to be simulated; and calculating positions of the multiple atoms to be simulated at each time in a second time series by utilizing the improved generative adversarial network.

According to another aspect of the present disclosure, a device for simulating atomic dynamics is provided. The device includes a memory and one or more processors. The processor is configured to: set initial positions for multiple specific atoms in a specific scene; calculate, based on the initial positions, positions of the multiple specific atoms at each time in a first time series by utilizing an LAMMPS configured with respect to the specific scene, as real positions; calculate, based on the initial positions, positions of the multiple specific atoms at each time in the first time series by utilizing a generative adversarial network, as predicted positions; improve a configuration of the generative adversarial network based on the real position and the predicted position at the same time; set initial positions for multiple atoms to be simulated; and calculate positions of the multiple atoms to be simulated at each time in a second time series by utilizing the improved generative adversarial network.

According to another aspect of the present disclosure, a recording medium having stored thereon a program is provided. The program, when executed by a computer, causes the computer to perform the method for simulating atomic dynamics described above.

DETAILED DESCRIPTION OF EMBODIMENTS

Figure 1:
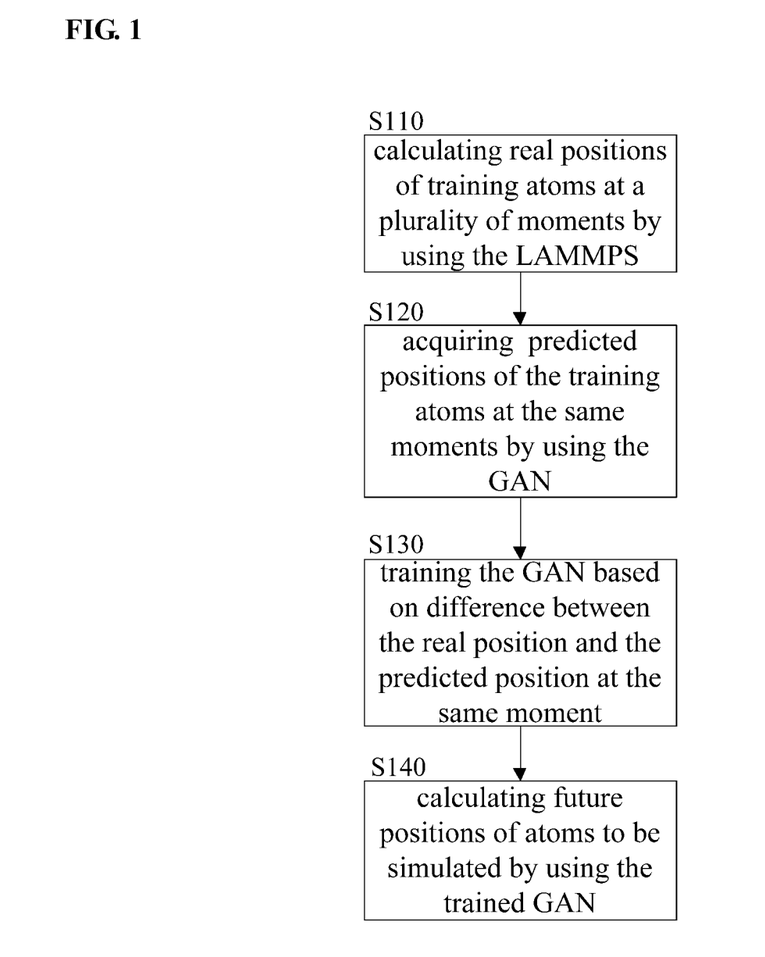
FIG. 1 is a general flowchart showing a method of simulating atomic dynamics according to the present disclosure.

FIG. 1 is a general flowchart showing a method of simulating atomic dynamics according to the present disclosure.

As shown in FIG. 1, a generative adversarial network (GAN) is trained by performing steps S110 to S130, and the trained GAN is applied in actual simulations in step S140. For clarity, an atom in the training phase is hereinafter referred to as "training atom", and an atom in the actual simulation phase is hereinafter referred to as "atom to be simulated".

Specifically, in step S110, positions of training atoms at a plurality of moments after an initial moment are calculated by utilizing the LAMMPS, as real positions of the training atoms at the corresponding moments. In the present disclosure, a position of an atom may be represented by a three-dimensional coordinate of the atom. Preferably, the three-dimensional coordinate of the atom is normalized within an interval of [0, 1].

In step S120, positions of the training atoms at the same moments are acquired by utilizing the GAN, as predicted positions of the training atoms at the corresponding moments. The GAN may be implemented with a deep neural network.

In step S130, the GAN is trained based the real position and the predicted position of the training atom at the same moment.

Next, in step S140, positions of atoms which are actual simulation targets at future moments are calculated by utilizing the trained GAN. The position of the atom to be simulated at any future moment may be obtained from the calculation result, thereby obtaining the future movement state of the atom.

It should be noted that, in the present disclosure, the future position of an atom is an example of the atomic dynamics, and simulation of the atomic dynamics is not limited to simulation of the future position of the atom. For example, nuclear charge of the atom may be simulated.

As shown in FIG. 1, in the method according to the present disclosure, the atomic dynamics is simulated by utilizing a trained deep neural network, which has advantages of small amount of computations and low complexity in actual simulations, requiring fewer computing resources and less time compared with the conventional tool LAMMPS.

Figure 2:
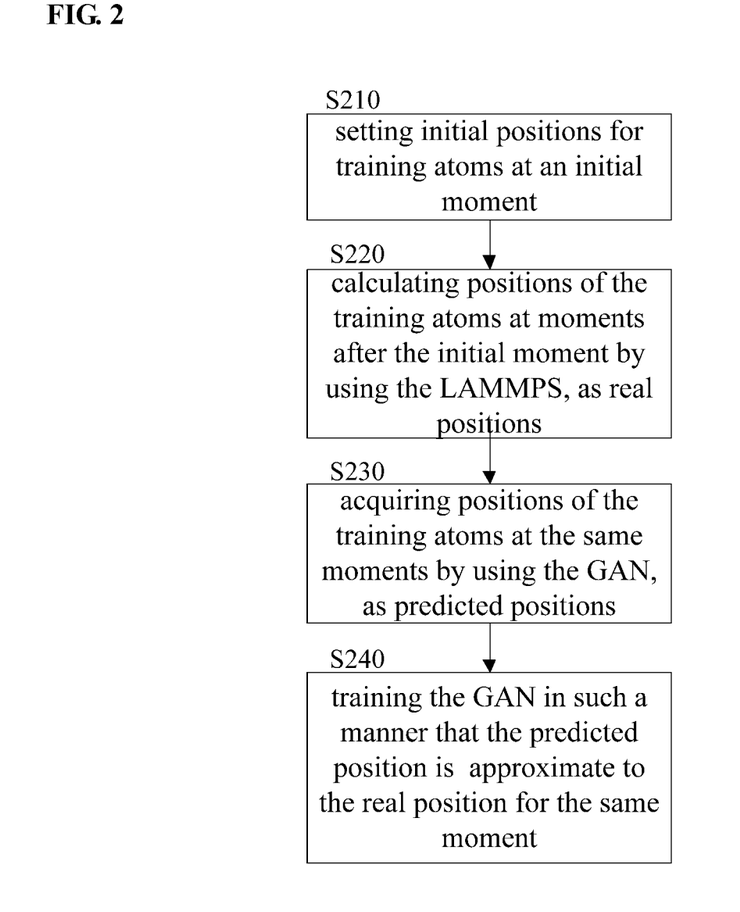
FIG. 2 is a flowchart showing a process of training a generative adversarial network.

The process of training the GAN is described in detail below with reference to FIGS. 2 to 4. FIG. 2 is a flowchart showing a process for training a GAN.

As shown in FIG. 2, in step S210, initial positions for multiple training atoms at an initial moment are set with respect to a specific scene. For example, in a case that microscopic properties of copper are simulated and studied, initial positions for multiple copper atoms are set based on states such as initial temperature, pressure and density.

In step S220, based on the initial positions, real positions of the multiple training atoms at a plurality of moments after the initial moment are calculated by utilizing the LAMMPS. For example, the plurality of moments may be set at a predetermined interval or may be set irregularly.

In step S230, predicted positions of the multiple training atoms at the same moments are calculated by utilizing the GAN based on the initial positions. Since the GAN has not yet been trained, the initial configuration of the GAN is applied.

Next, in step S240, the GAN is trained based on the real position and the predicted position at the same moment obtained in steps S220 and S230, such that the predicted position calculated by utilizing the GAN can be as close as possible to the real position calculated by utilizing the LAMMPS. The training for the GAN is completed when the predicted position can be deemed to be substantially the same as the real position.

Figure 3:
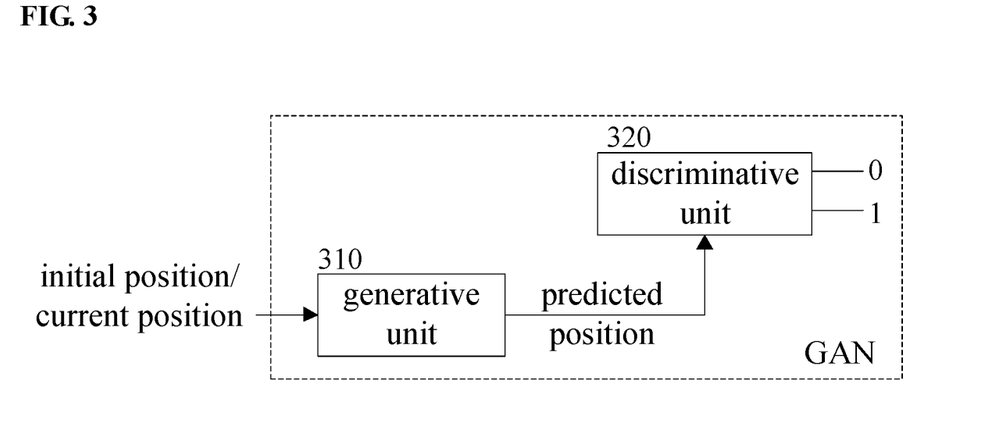
FIG. 3 is a schematic block diagram of the generative adversarial network.
Figure 4:
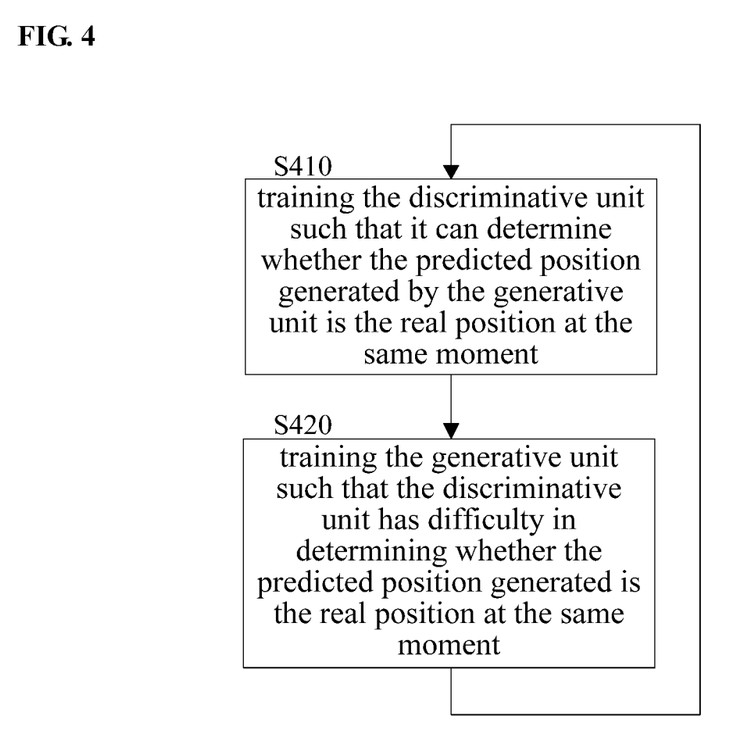
FIG. 4 shows a specific process of step S240 shown in FIG. 2.

FIG. 3 is a schematic block diagram of a GAN. FIG. 4 shows a specific process of step S240 shown in FIG. 2.

As shown in FIG. 3, the GAN includes a generative unit 310 and a discriminative unit 320. In the present disclosure, the generative unit 310 and the discriminative unit 320 may be implemented with neural networks. The generative unit 310 is configured to generate predicted positions for training atoms at the next moment based on the input initial positions (or current positions) of the training atoms. The discriminative unit 320 is configured to receive the predicted positions from the generative unit 310, and determine a probability that the received predicted position is the real position at the next moment. In a case that the determined probability is greater than 50%, the discriminative unit 320 outputs a determination result of "1" representing that the predicted position is the real position. In a case that the determined probability is less than 50%, the discriminative unit 320 outputs a determination result of "0" representing that the predicted position is not the real position.

The discriminative unit 320 makes efforts to determine whether the received predicted position is the real position at the same moment. If the determined probability is large (greater than 50%), the discriminative unit 320 is more convinced that the predicted position is the real position. If the determined probability is small (less than 50%), the discriminative unit 320 is more convinced that the predicted position is not the real position.

The generative unit 310 makes efforts to generate the predicted position as close as possible to the real position, so that the discriminative unit 320 has difficulty in distinguishing the predicted position from the real position. In other words, if the discriminative unit 320 has difficulty in determining whether the received predicted position is the real position, that is, if the probability determined by the discriminative unit 320 is 50% or approximate to 50%, the generative unit 310 reaches an ideal state.

The generative unit 310 and the discriminative unit 320 constituting the GAN are trained based on the objects as described above. As shown in FIG. 4, the discriminative unit 320 is firstly trained in step S410, so that the discriminative unit 320 is capable of determining whether the predicted position received from the generative unit 310 is the real position at the same moment, i.e., such that the discriminative unit 320 is capable of determining whether the probability is greater than 50% or less than 50%.

It is assumed that the number of training atoms is m, and real positions of the m training atoms calculated by utilizing the LAMMPS are expressed as $x^1, x^2, \ldots, x^m$ respectively. The discriminative unit 320 may be trained in a manner of maximizing the following loss function $L_D$.

$$L_D = \frac{1}{m} \sum_{i=1}^{m} [\log D(x^i) + \log(1 - D(G(x^i)))] \qquad (1)$$

wherein $x^i$ represents a real position of an i-th training atom (i=1, 2, ..., m), $G(x^i)$ represents predicted position of the i-th training atom generated by the generative unit 310, and D ( ) represents a probability that a position indicated by the term within the parentheses is the real position.

Then, the generative unit 310 is trained in step S420, so that the discriminative unit 320 has difficulty in determining whether the predicted position generated by the generative unit 310 is the real position at the same moment, i.e., so that the probability determined by the discriminative unit 320 is 50% or approximate to 50%.

Specifically, the generative unit 310 may be trained in a manner of minimizing the following loss function $L_G$.

$$L_G = \frac{1}{m} \left( L_{MSE} + \lambda \cdot \sum_{i=1}^{m} \log(1 - D(G(x^i))) \right) \qquad (2)$$

wherein $G(x^i)$ represents predicted position of the i-th training atom generated by the generative unit 310, $D(G(x^i))$ represents a probability determined by the discriminative unit 320 that the predicted position is the real position, $L_{MSE}$ represents mean square error between the real position and the predicted position at the same moment, and $\lambda$ represents a weighting parameter which may be set as for example 0.5 or 1. It can be seen from the formula (2) that the mean square error $L_{MSE}$ is required to be minimized in order to minimize the loss function $L_G$. Further, the $L_{MSE}$ may be calculated from the following formula (3).

$$L_{MSE} = \Sigma_{i=1}^{m}(x^i - G(x^i))^2 \qquad (3)$$

The generative unit 310 and the discriminative unit 320 may be alternately and iteratively trained by repeatedly performing steps S410 and S420. In a case that the probability determined by the discriminative unit 320 is 50% or approximate to 50%, it is indicated that the discriminative unit 320 has difficulty in distinguishing the predicted position from the real position. In this case, the predicted position generated by the generative unit 310 can be considered to be the same as the real position calculated by utilizing the LAMMPS. Since the generative unit 310 is capable of generating the same output as the LAMMPS, the generative unit 310 can be applied in actual simulations to take place of the LAMMPS. As such, the training for the GAN is completed.

Figure 5:
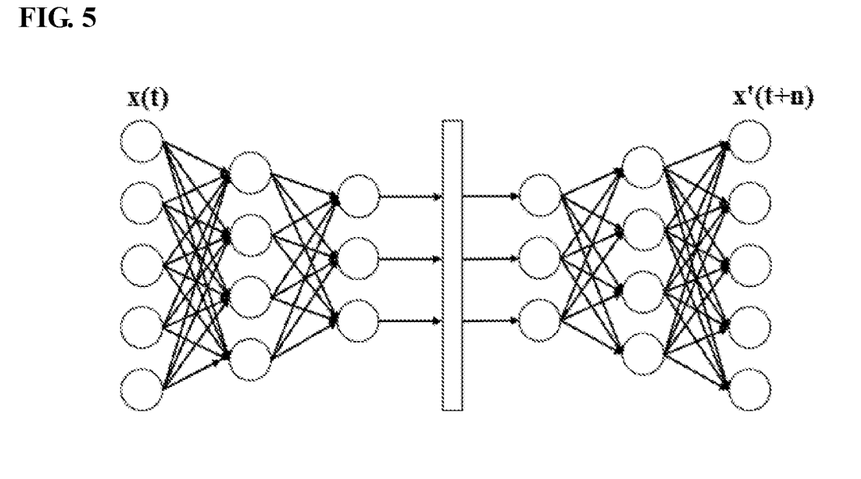
FIG. 5 schematically shows a generative unit implemented with a neural network.
Figure 6:
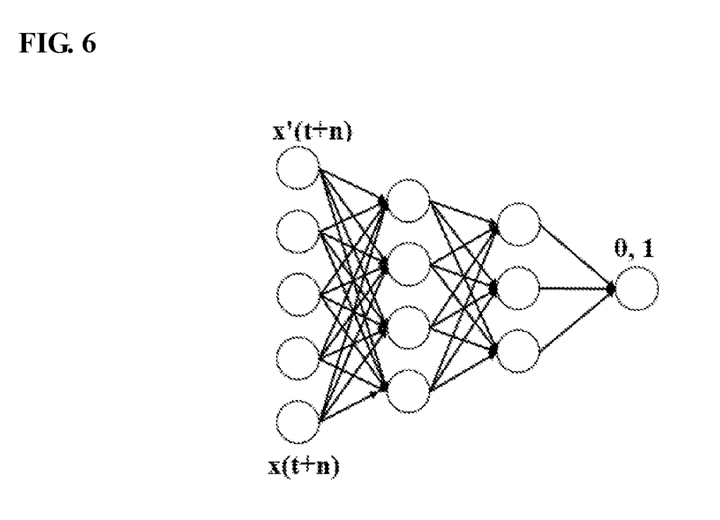
FIG. 6 schematically shows a discriminative unit implemented with a neural network.

FIGS. 5 and 6 respectively schematically show neural network structures of the generative unit 310 and the discriminative unit 320, in which a circle represents a neural cell. As shown in FIG. 5, a position coordinate x(t) of an atom at time t is input at an input end of the generative unit 310, and a predicted position coordinate x'(t+n) of the atom at time t+n is output at an output end of the generative unit 310. As shown in FIG. 6, the predicted position coordinate x'(t+n) output by the generative unit 310 and a real position coordinate x(t+n) of the atom at time t+n calculated by the LAMMPS are input at an input end of the discriminative unit 320, and a determination result "0" or "1" is output at an output end of the discriminative unit 320.

It should be noted that, as described in the above, the position of the atom is just an example of the atomic dynamics, and simulating the atomic dynamics is not limited to simulating the future position of the atom. For example, properties such as the nuclear charge of the atom may also be simulated. Therefore, the position coordinates such as x(t) and x'(t+n) shown in FIGS. 5 and 6 may be extended to include other properties of the atom.

Figure 7:
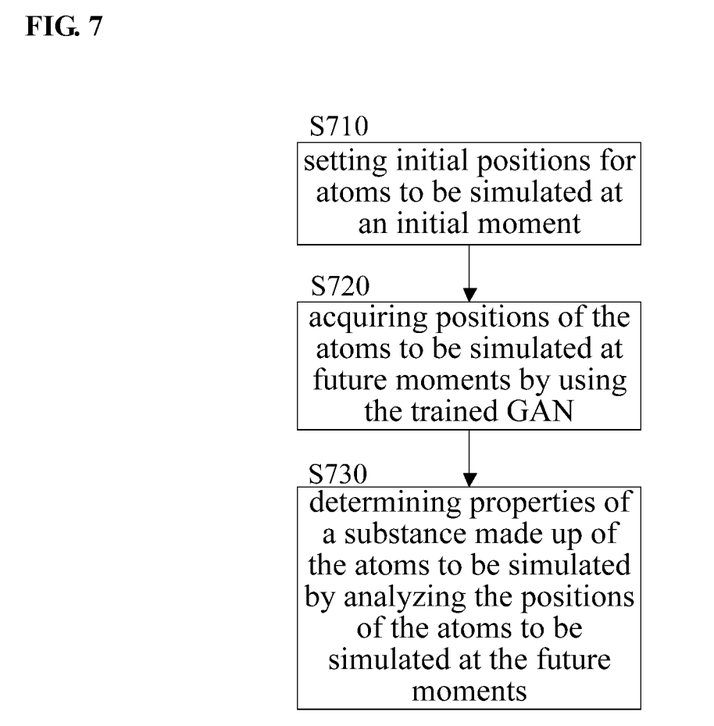
FIG. 7 is a flowchart showing a process of simulating atomic dynamics by utilizing the trained generative adversarial network.

The process of applying the trained GAN in actual simulations is described below with reference to FIG. 7, which is a flowchart showing a process of simulating atomic dynamics by utilizing the trained GAN.

In step S710, initial positions of multiple atoms which are actual simulation targets at an initial moment are set. Next, in step S720, positions of atoms to be simulated at one or more moments after the initial moment are acquired by utilizing the trained GAN based on the initial positions, as the simulation result. The one or more moments at which the simulation result is expected may be set based on practical requirements.

In step S730, properties of a substance made up of the atoms are determined by analyzing the simulation result. For example, it is assumed that positions of multiple copper atoms at a plurality of moments are acquired as the simulation result in step S720. Information on the copper atoms, such as movement track, movement direction and speed, may be obtained by analyzing the positions of the copper atoms at the moments in step S730, thereby obtaining properties of copper made up of the copper atoms, such as temperature, form and density.

Technical solutions of the present disclosure are described above in combination with the embodiments. With the technical solutions of the present disclosure, the trained GAN can produce the same simulation result as the LAMMPS, which has advantages of small amount of computations and low complexity in actual applications, requiring fewer computing resources and less time.

The method described in the above embodiments may be performed by software, hardware, or a combination of software and hardware. Programs included in the software may be stored in advance in a storage medium provided inside or outside the device. As an example, during execution, these programs are written to a random-access memory (RAM) and executed by a processor (such as CPU), so as to perform the processes described herein.

Figure 8:
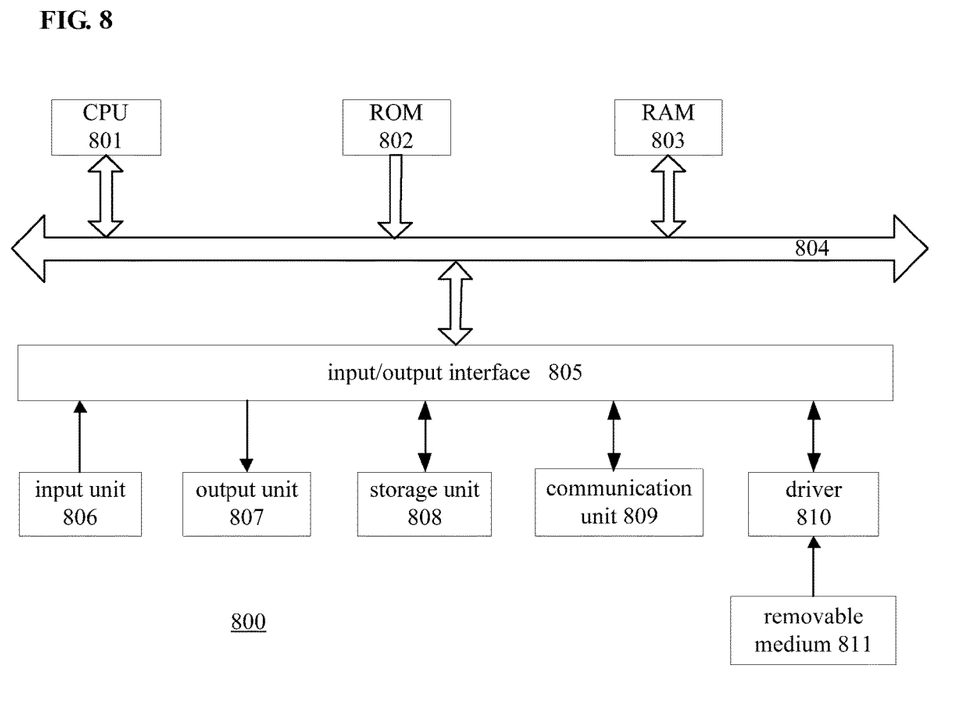
FIG. 8 is a block diagram showing a configuration example of computer hardware for implementing the present disclosure.

FIG. 8 is a block diagram showing a configuration example of computer hardware for performing the method according to the present disclosure based on programs. The computer hardware is an example of the device for simulating atomic dynamics according to the present disclosure.

As shown in FIG. 8, in a computer 800, a central processing unit (CPU) 801, a read-only memory (ROM) 802, and a random-access memory (RAM) 803 are connected to each other via a bus 804.

An input/output interface 805 is further connected to the bus 804. The input/output interface 805 is connected with the following components: an input unit 806 including keyboard, mouse, microphone and the like; an output unit 807 including display, speaker and the like; a storage unit 808 including hard disk, nonvolatile memory and the like; a communication unit 809 including network interface card (such as local area network (LAN) card, modem); and a driver 810 that drives a removable medium 811 such as magnetic disk, optical disk, magneto-optical disk, or semiconductor memory.

In the computer having the above configuration, the CPU 801 loads a program stored in the storage unit 808 into the RAM 803 via the input/output interface 805 and the bus 804, and executes the program so as to perform the method described above.

A program to be executed by the computer (CPU 801) may be recorded on the removable medium 811 as a package medium including a magnetic disk (including floppy disk), an optical disk (including compact disk-read only memory (CD-ROM)), digital versatile disk (DVD), and the like), a magneto-optical disk, or a semiconductor memory, and the like. In addition, the program to be executed by the computer (CPU 801) may also be provided via wired or wireless transmission medium, such as local area network, the Internet, or digital satellite broadcast.

In a case where the removable medium 811 is installed in the driver 810, the program may be installed in the storage unit 808 via the input/output interface 805. In addition, the program may be received by the communication unit 809 via the wired or wireless transmission medium, and then the program may be installed in the storage unit 808. Alternatively, the program may be installed in the ROM 802 or the storage unit 808 in advance.

The program to be executed by the computer may be a program that executes the process according to the order described in the present specification or may be a program that executes the process in parallel or executes the process when needed (for example, when called).

Units or devices described herein are merely logical in nature and do not strictly correspond to physical devices or entities. For example, the functionality of each unit described herein may be implemented by multiple physical entities or the functionality of multiple units described herein may be implemented by a single physical entity. In addition, it should be noted that features, components, elements or steps, and the like described in an embodiment are not limited to this embodiment, but may also be applied to other embodiments, for example, may substitute for specific features, components, elements, or steps, and the like in other embodiments or may be combined with them.

The scope of the present disclosure is not limited to those embodiments described herein. It should be understood by those skill in the art that various modifications or changes in the embodiments discussed herein can be made without departing from the spirit and principle of the present disclosure, depending on design requirements and other factors. The scope of the present disclosure is defined by the appended claims and their equivalents.

According to aspects of embodiments, (1) A method for simulating atomic dynamics, including:
setting initial positions for multiple specific atoms in a specific scene;
calculating, based on the initial positions, positions of the multiple specific atoms at each time in a first time series by utilizing a Large-scale Atomic/Molecular Massively Parallel Simulator (LAMMPS) configured with respect to the specific scene, as real positions;
calculating, based on the initial positions, positions of the multiple specific atoms at each time in the first time series by utilizing a generative adversarial network, as predicted positions;
improving a configuration of the generative adversarial network based on the real position and the predicted position at the same time;
setting initial positions for multiple atoms to be simulated; and
calculating positions of the multiple atoms to be simulated at each time in a second time series by utilizing the improved generative adversarial network.

(2) The method according to (1), further including:
calculating the predicted positions of the multiple specific atoms at each time in the first time series by utilizing a generative unit in the generative adversarial network;
determining a probability that the predicted position is the real position at the same time by utilizing a discriminative unit in the generative adversarial network; and
improving configurations of the generative unit and the discriminative unit based on the predicted position and the real position at the same time, until the probability determined by the discriminative unit is 50%.

(3) The method according to (2), further including:
improving the discriminative unit in such a manner that the discriminative unit is capable of determining whether the predicted position is the real position at the same time.

(4) The method according to (3), further including:
improving the generative unit in such a manner that the discriminative unit has difficulty in determining whether the predicted position calculated by the generative unit is the real position at the same time.

(5) The method according to (3), further including:
improving the generative unit in a manner of minimizing mean square error between the real position and the predicted position at the same time.

(6) The method according to (1), further including:
determining properties of a substance made up of the multiple atoms to be simulated by analyzing the positions of the multiple atoms to be simulated at each time in the second time series.

(7) The method according to (1), wherein the generative unit and the discriminative unit are implemented with neural networks.

(8) A device for stimulating atomic dynamics, including:
a memory, and one or more processors configured to:
set initial positions for multiple specific atoms in a specific scene;
calculate, based on the initial positions, positions of the multiple specific atoms at each time in a first time series by utilizing a Large-scale Atomic/Molecular Massively Parallel Simulator (LAMMPS) configured with respect to the specific scene, as real positions;
calculate, based on the initial positions, positions of the multiple specific atoms at each time in the first time series by utilizing a generative adversarial network, as predicted positions;
improve a configuration of the generative adversarial network based on the real position and the predicted position at the same time;
set initial positions for multiple atoms to be simulated; and
calculate positions of the multiple atoms to be simulated at each time in a second time series by utilizing the improved generative adversarial network.

(9) The device according to (8), wherein the processor is further configured to:
calculate the predicted positions of the multiple specific atoms at each time in the first time series by utilizing a generative unit in the generative adversarial network;
determine a probability that the predicted position is the real position at the same time by utilizing a discriminative unit in the generative adversarial network; and
improve configurations of the generative unit and the discriminative unit based on the predicted position and the real position at the same time, until the probability determined by the discriminative unit is 50%.

(10) The device according to (9), wherein the processor is further configured to:
improve the discriminative unit in such a manner that the discriminative unit is capable of determining whether the predicted position is the real position at the same time; and
improve the generative unit in such a manner that the discriminative unit has difficulty in determining whether the predicted position calculated by the generative unit is the real position at the same time.

(11) A recording medium having stored thereon a program that, when executed by a computer, causes the computer to perform the method for simulating atomic dynamics according to any one of (1) to (7).

The invention claimed is:

1. A method for a computer to simulate atomic dynamics, comprising:
setting initial positions for a plurality of specific atoms in a specific scene;
calculating, based on the initial positions, positions of the plurality of specific atoms at each time in a first time series in the specific scene to represent real positions by utilizing a software tool known as LAMMPS (Large-scale Atomic/Molecular Massively Parallel Simulator) configured with respect to the specific scene;
calculating, based on the initial positions, positions of the plurality of specific atoms at the same time in the first time series in the specific scene to represent predicted positions by utilizing a generative adversarial network (GAN);
training a configuration of the GAN based on the real positions and the predicted positions at the same time;
setting initial positions for a plurality of atoms to be simulated in a scene;

calculating positions of the plurality of atoms simulated in the scene at each time in a second time series by utilizing the trained GAN;

determining movement information of the plurality of atoms simulated by analyzing the positions of the plurality of atoms simulated at each time in the second time series; and determining properties of a substance made up of the plurality of atoms simulated based on the movement information.

2. The method according to claim 1, further comprising:
calculating the predicted positions of the plurality of specific atoms at the same time in the first time series by utilizing a generative unit in the GAN;

determining a probability that a predicted position among the predicted positions is a real position among the real positions at the same time by utilizing a discriminative unit in the GAN; and training the configuration of the generative unit and the discriminative unit based on the predicted position and the real position at the same time, until the probability determined by the discriminative unit is 50%.

3. The method according to claim 2, further comprising:
training the discriminative unit in such a manner that the discriminative unit is capable of determining whether the predicted position is the real position at the same time.

4. The method according to claim 3, further comprising:
training the generative unit in such a manner that the discriminative unit is not capable of determining whether the predicted position calculated by the generative unit is the real position at the same time.

5. The method according to claim 3, further comprising:
training the generative unit in a manner of minimizing a mean square error between the real position and the predicted position at the same time.

6. The method according to claim 1, wherein the generative unit and the discriminative unit are implemented with neural networks.

7. A device to simulate atomic dynamics, the device comprising:
a memory, and a processor configured to:
set initial positions for a plurality of specific atoms in a specific scene;
calculate, based on the initial positions, positions of the plurality of specific atoms at each time in a first time series in the specific scene to represent real positions by utilizing a software tool known as LAMMPS (Large-scale Atomic/Molecular Massively Parallel Simulator) configured with respect to the specific scene;
calculate, based on the initial positions, positions of the plurality of specific atoms at the same time in the first time series in the specific scene to represent predicted positions by utilizing a generative adversarial network (GAN);
train a configuration of the GAN based on the real positions and the predicted positions at the same time;
set initial positions for a plurality of atoms to be simulated in a scene;
calculate positions of the plurality of atoms simulated in the scene at each time in a second time series by utilizing the trained GAN;
determine movement information of the plurality of atoms simulated by analyzing the positions of the plurality of atoms to be simulated at each time in the second time series; and
determine properties of a substance made up of the plurality of atoms simulated based on the movement information.

8. The device according to claim 7, wherein the processor is further configured to:
calculate the predicted positions of the plurality of specific atoms at the same time in the first time series by utilizing a generative unit in the GAN;
determine a probability that a predicted position among the predicted positions is a real position among the real positions at the same time by utilizing a discriminative unit in the GAN; and
train the configuration of the generative unit and the discriminative unit based on the predicted position and the real position at the same time, until the probability determined by the discriminative unit is 50%.

9. The device according to claim 8, wherein the processor is further configured to:
train the discriminative unit in such a manner that the discriminative unit is capable of determining whether the predicted position is the real position at the same time; and
train the generative unit in such a manner that the discriminative unit is not capable of determining whether the predicted position calculated by the generative unit is the real position at the same time.

* * * * *